(12) United States Patent
Desai et al.

(10) Patent No.: US 10,420,571 B2
(45) Date of Patent: Sep. 24, 2019

(54) SPECIMEN RETRIEVAL SYSTEM

(71) Applicant: DeRoyal Industries, Inc., Powell, TN (US)

(72) Inventors: Dhanvin Desai, Knoxville, TN (US); Scott Barnes, Knoxville, TN (US); Lee Freeman, Knoxville, TN (US); Mike Kastura, Knoxville, TN (US)

(73) Assignee: DeRoyal Industries, Inc., Powell, TN (US)

( * ) Notice: Subject to any disclaimer, the term of this patent is extended or adjusted under 35 U.S.C. 154(b) by 263 days.

(21) Appl. No.: 15/495,467

(22) Filed: Apr. 24, 2017

(65) Prior Publication Data

US 2017/0311964 A1 Nov. 2, 2017

Related U.S. Application Data

(60) Provisional application No. 62/330,460, filed on May 2, 2016.

(51) Int. Cl.
*A61B 17/221* (2006.01)

(52) U.S. Cl.
CPC .... *A61B 17/221* (2013.01); *A61B 2017/2212* (2013.01)

(58) Field of Classification Search
CPC ........... A61B 2017/00287; A61B 2017/00867; A61B 2017/2212; A61B 2017/2918;
(Continued)

(56) References Cited

U.S. PATENT DOCUMENTS 5,403,324 A * 4/1995 Ciervo ............ A61B 17/22012
604/264
6,409,733 B1 6/2002 Conlon et al.
(Continued)

OTHER PUBLICATIONS

Espiner Medical Ltd, Master E-Sac, EcoSac, Standard E-Sac, Super E-Sac, http://espinermedical.com/index.php/esacs/ The dates of this publication is not known, but it is requested that it be considered as prior art for purposes of examination.
(Continued)

*Primary Examiner* — Ryan J. Severson
*Assistant Examiner* — Mohamed G Gabr
(74) *Attorney, Agent, or Firm* — Luedeka Neely Group, PC

(57) ABSTRACT

A specimen retrieval system includes a bag having a flexible basket with an opening configured for receiving a tissue specimen, an elongate tail extending from the flexible basket, a primary loop attached to a proximal end of the tail opposite the flexible basket, and a string encircling the flexible basket and extending therefrom along the tail and terminating exterior of the proximal end of the tail, the string being operable to close the opening of the flexible basket. The system also includes an outer cannula having a distal end and a proximal end with a cannula handle located at the proximal end of the outer cannula, the outer cannula configured to receive the bag therein via the distal end of the outer cannula, with the tail of the bag, the primary loop and a portion of the string extending out of the proximal end of the outer cannula. The system also includes an interior tube having a distal end slidably positionable within the outer cannula via the proximal end of the outer cannula, the interior tube having a tube handle mounted to a proximal end of the interior tube at a location exterior of the cannula handle, the tube handle including a hook rotatably mounted thereon and configured for engaging the primary loop of the
(Continued)

bag when rotated to a first position and configured for disengaging from the primary loop when rotated to a second position, and a spring secured within the distal end of the interior tube and extending outwardly of the distal end of the interior tube, the spring connectable to the opening of the basket of the bag.

9 Claims, 17 Drawing Sheets

(58) Field of Classification Search
CPC .... A61B 2017/2924; A61B 2017/2927; A61B 2017/00336; A61B 2017/294; A61B 2017/2946; A61B 17/00234; A61B 17/221; A61B 17/30; A61B 17/00; A61B 17/0293; A61B 17/32056; A61B 10/04; A61F 2002/2484; A61F 2/2481; A61M 1/008
See application file for complete search history.

(56) References Cited

U.S. PATENT DOCUMENTS

| | | |
|---|---|---|
| 8,075,567 B2 | 12/2011 | Taylor et al. |
| 8,827,968 B2 | 9/2014 | Taylor et al. |
| 8,870,894 B2 | 10/2014 | Taylor et al. |
| D731,052 S | 6/2015 | Doerr et al. |
| 2007/0073251 A1 | 3/2007 | Zhou et al. |
| 2009/0182292 A1* | 7/2009 | Egle ................. A61B 17/00234 604/327 |
| 2011/0184433 A1* | 7/2011 | Parihar ............ A61B 17/00234 606/114 |
| 2013/0023895 A1 | 1/2013 | Saleh |

OTHER PUBLICATIONS

Genicon, Winter Park, FL U.S.A., Genistrong Specimen Retrieval Bag, www.geniconendo.com; The dates of this publication is not known, but it is requested that it be considered as prior art for purposes of examination.
International Searching Authority, International Search Report and Written Opinion, PCT/US2017/030416 dated Jul. 19, 2017.

* cited by examiner

SPECIMEN RETRIEVAL SYSTEM

FIELD

This application claims priority to U.S. Provisional Application No. 62/330,460 filed May 2, 2016, entitled SPECIMEN RETRIEVAL SYSTEM, incorporated herein by reference in its entirety.

FIELD

The present disclosure relates to a medical specimen retrieval system. More particularly, the disclosure relates to a specimen retrieval system for use in laparoscopic surgery.

BACKGROUND

Improvement is desired in the construction of medical specimen retrieval devices of the type utilizing a specimen bag for retrieving tissue specimens during laproscopic surgery.

In particular, what is desired is a retrieval system configured to facilitate one-handed operation of the retrieval system.

The disclosure advantageously provides a specimen retrieval system for use during laparoscopic surgery to assist in the retrieval and removal of tissue.

SUMMARY

The disclosure relates to a specimen retrieval system.

In one aspect, the specimen retrieval system includes a bag having a flexible basket with an opening configured for receiving a tissue specimen, an elongate tail extending from the flexible basket, a primary loop attached to a proximal end of the tail opposite the flexible basket, and a string encircling the flexible basket and extending therefrom along the tail and terminating exterior of the proximal end of the tail, the string being operable to close the opening of the flexible basket.

The system also includes an outer cannula having a distal end and a proximal end with a cannula handle located at the proximal end of the outer cannula, the outer cannula configured to receive the bag therein via the distal end of the outer cannula, with the tail of the bag, the primary loop and a portion of the string extending out of the proximal end of the outer cannula.

The system also includes an interior tube having a distal end slidably positionable within the outer cannula via the proximal end of the outer cannula, the interior tube having a tube handle mounted to a proximal end of the interior tube at a location exterior of the cannula handle, the tube handle including a hook rotatably mounted thereon and configured for engaging the primary loop of the bag when rotated to a first position and configured for disengaging from the primary loop when rotated to a second position, and a spring secured within the distal end of the interior tube and extending outwardly of the distal end of the interior tube, the spring connectable to the opening of the basket of the bag.

The system is advantageously configured to enable one-handed operation to facilitate deployment of the flexible basket and retrieval and closure of the flexible basket using only one hand.

In another aspect, the specimen retrieval system includes A bag having a flexible basket with an opening configured for receiving a tissue specimen, an elongate tail extending from the flexible basket, a user engagement structure attached to a proximal end of the tail opposite the flexible basket and configured for being engaged by a user, and a string encircling the flexible basket and extending therefrom along the tail and terminating exterior of the proximal end of the tail, the string being operable to close the opening of the flexible basket.

The system also includes an outer cannula having a distal end and a proximal end with a cannula handle located at the proximal end of the outer cannula, the outer cannula configured to receive the bag therein via the distal end of the outer cannula, with the tail of the bag, the primary loop and a portion of the string extending out of the proximal end of the outer cannula.

The system further includes an interior tube having a distal end slidably positionable within the outer cannula via the proximal end of the outer cannula, the interior tube having a tube handle mounted to a proximal end of the interior tube at a location exterior of the cannula handle, and a spring secured within the distal end of the interior tube and extending outwardly of the distal end of the interior tube, the spring connectable to the opening of the basket of the bag.

BRIEF DESCRIPTION OF THE DRAWINGS

Further advantages of the disclosure are apparent by reference to the detailed description when considered in conjunction with the figures, which are not to scale so as to more clearly show the details, wherein like reference numbers indicate like elements throughout the several views, and wherein.

DETAILED DESCRIPTION

Figure 1:
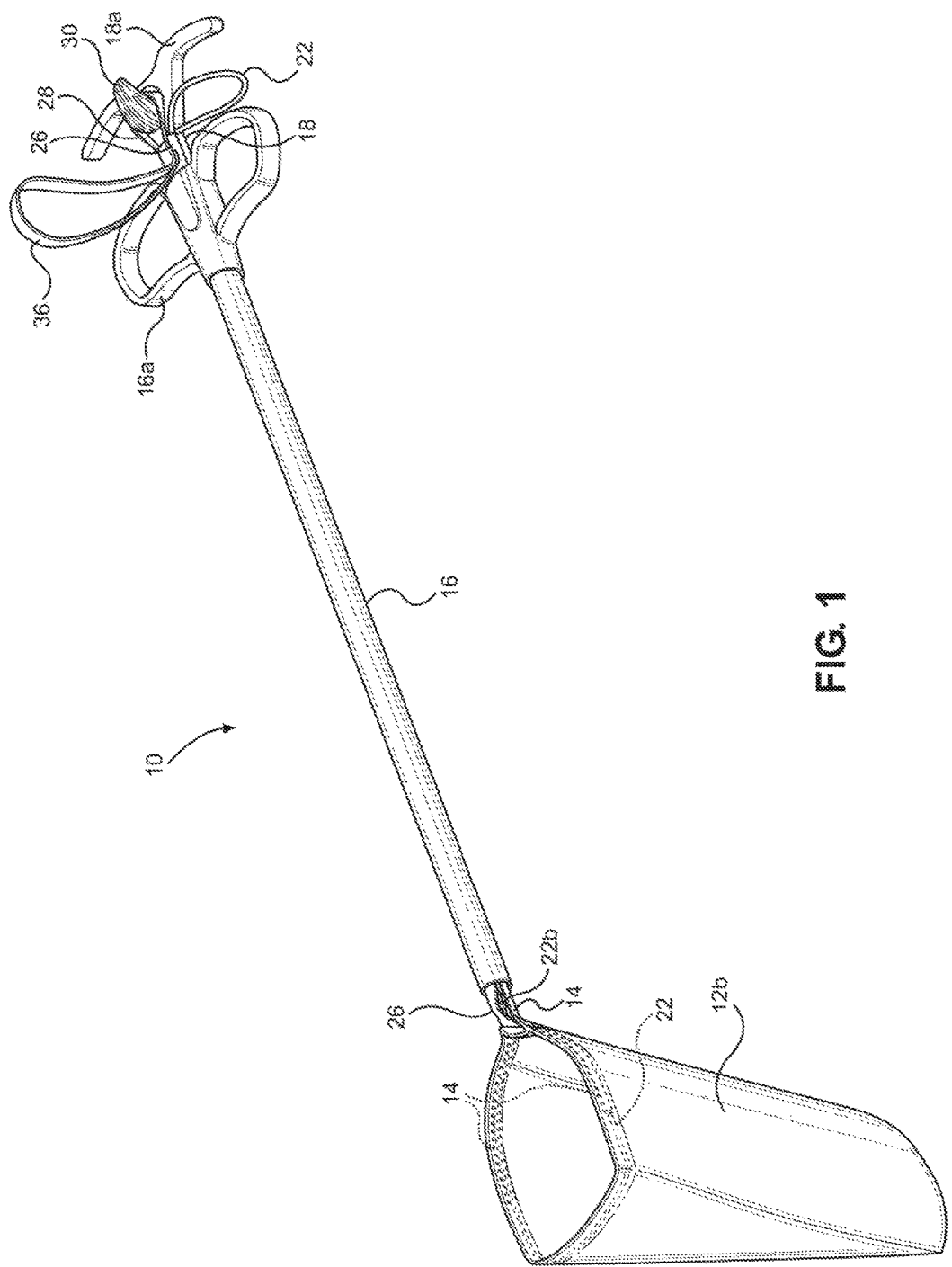
FIG. 1 is a perspective view of a specimen retrieval system according to the disclosure.

With reference to the drawings, the disclosure relates to a specimen retrieval system 10 for use during laparoscopic surgery to assist in the retrieval of compromised tissue. The retrieval system is configured to be used with a trocar system and includes a specimen bag 12, springs 14, an outer cannula 16 with a handle 16a configured to provide a pair of rings, an interior tube 18 with a handle 18a, a seal such as gasket or O-ring 20 (FIG. 17), and a string 22 configured for closing of the bag 12.

In general overview, laproscopic surgery typically involves forming three or more incisions. Small tubes or trocars are placed through these incisions and into the abdomen. Carbon dioxide gas is used to inflate the abdomen and a camera attached to a thin metal telescope or laparoscope is used to view the surgical site. Laproscopic instruments are passed through one or more of the trocars to perform the surgical procedure. take the place of the surgeon's hands and traditional surgical instruments. As part of this, care is taken so that all tissue cut during the procedure, including any tissue of interest (the specimen) is removed from the patient.

The specimen retrieval system 10 according to the disclosure is used in this capacity to remove tissue from the surgical site. Thus, the system 10 utilizes the bag 12 configured to be passed through a trocar, expanded within the surgical site, then retracted and removed via the trocar, all the while containing all tissue and fluids collected in the bag. In many cases, the bag 12 is deployed and retrieved multiple times during a surgical procedure.

Figure 2:
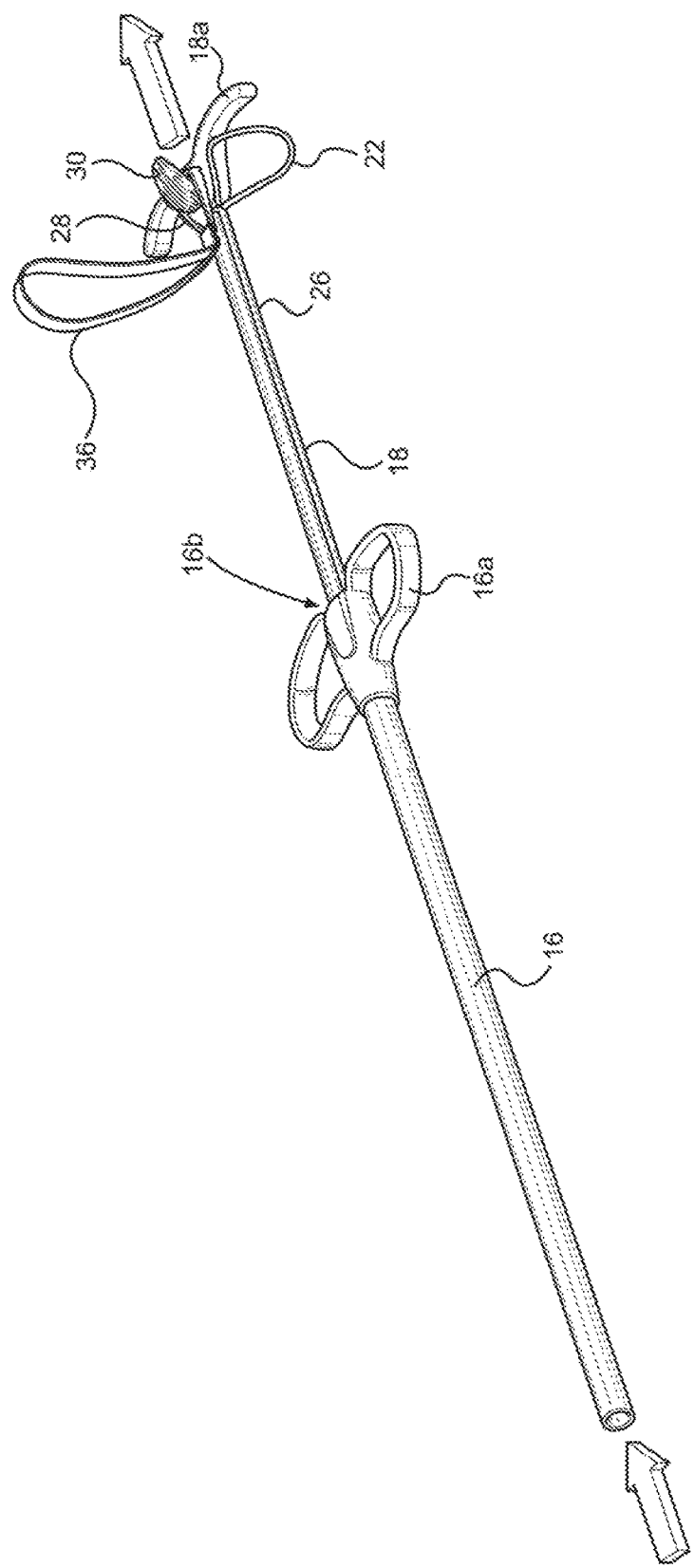
FIG. 2 shows initial retraction of a bag component during use of the specimen retrieval system of FIG. 1.
Figure 3:
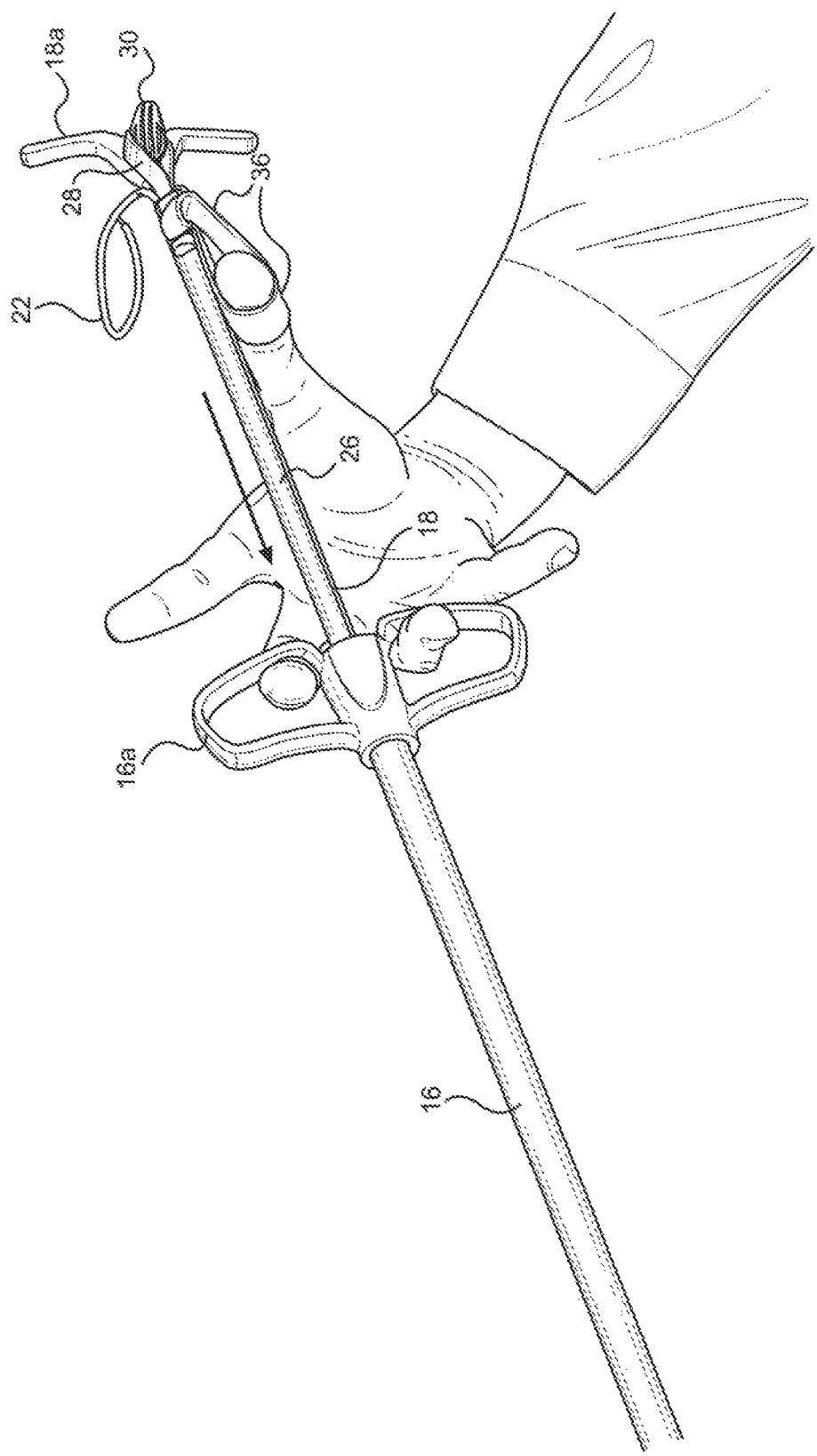
FIGS. 3 and 4 illustrate single handed bag deployment during use of the specimen retrieval system of FIG. 1.
Figure 4:
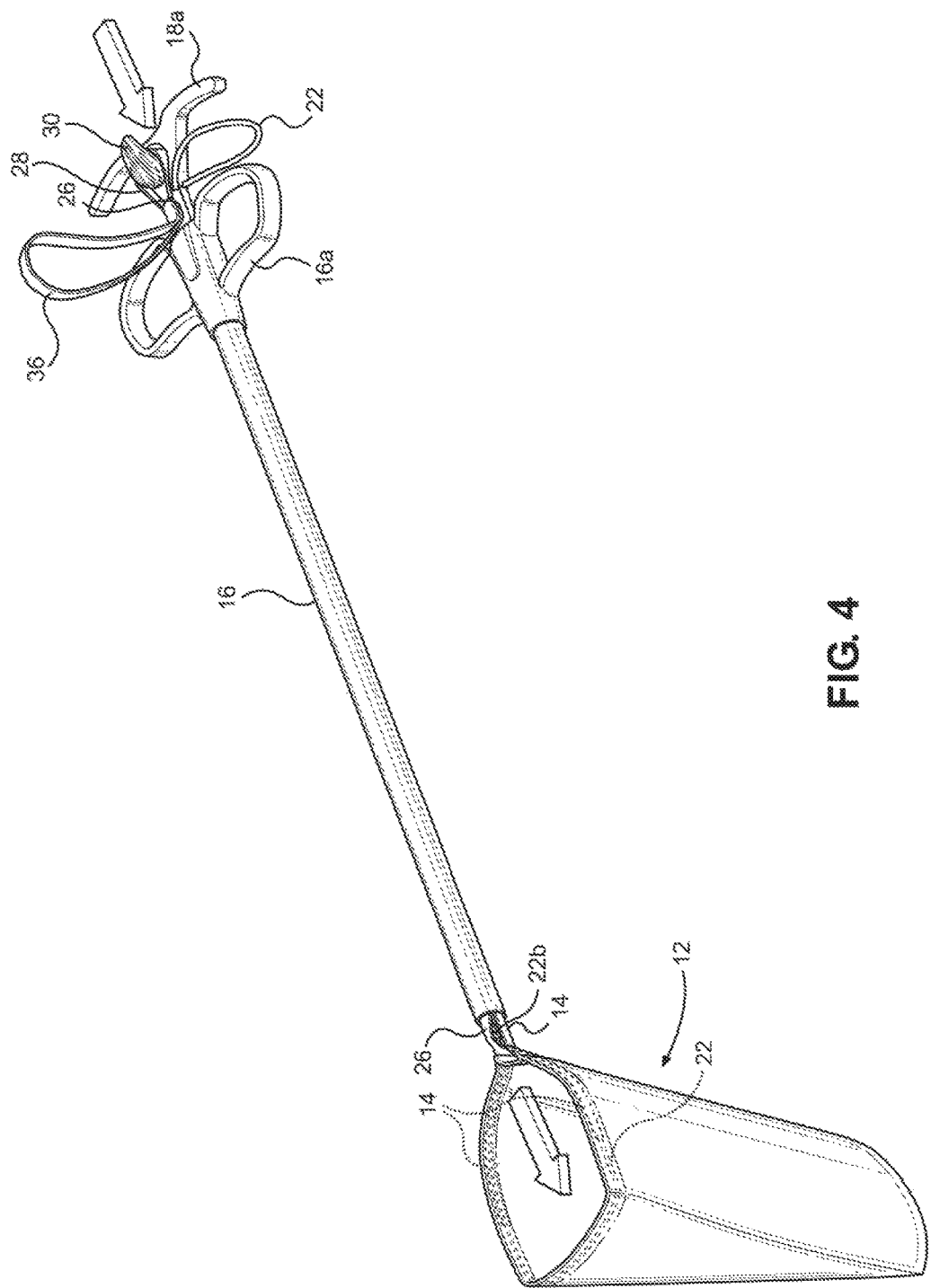

FIG. 1 shows the retrieval system as provided to the surgeon. Initially, in order to configure the system so that the bag 12 may be transported to the surgical site through a trocar, the bag 12 is first retracted as depicted in FIG. 2. Then, as shown in FIGS. 3 and 4, the bag 12 is deployed via a trocar to the surgical site by the surgeon. In this regard, one significant aspect of the retrieval system is that, once the bag 12 has been retracted for initial deployment into the surgical site, the system 10 is configured to enable single handed deployment of the bag 12. This is highly advantageous and described more fully below.

During use of the retrieval system 10, tissue from the surgical procedure is dropped or otherwise deposited inside the bag 12, then the bag 12 and tissue are retrieved simultaneously. The bag 12 is desirably made from a durable material and configured to hold a seal to prevent any parts of the compromised tissue spilling back into the patient.

The bag 12 is configured to provide a flexible basket structure and may be made with a translucent rip stop nylon material with a polyurethane inner lining. The rip stop nylon provides durability while the polyurethane allows the bag 12 to be radio frequency welded or heat sealed. The bag 12 is also made to be translucent so the general shape of the tissue can be visualized while still in the bag 12. The bag 12 includes a chase 12a located and extending around the upper perimeter of the bag 12. The chase 12a is sized and configured for receiving the springs 14 and the string 22. The bag 12 defines a flexible basket 12b configured for receiving tissue, specimens and the like.

Figure 7:
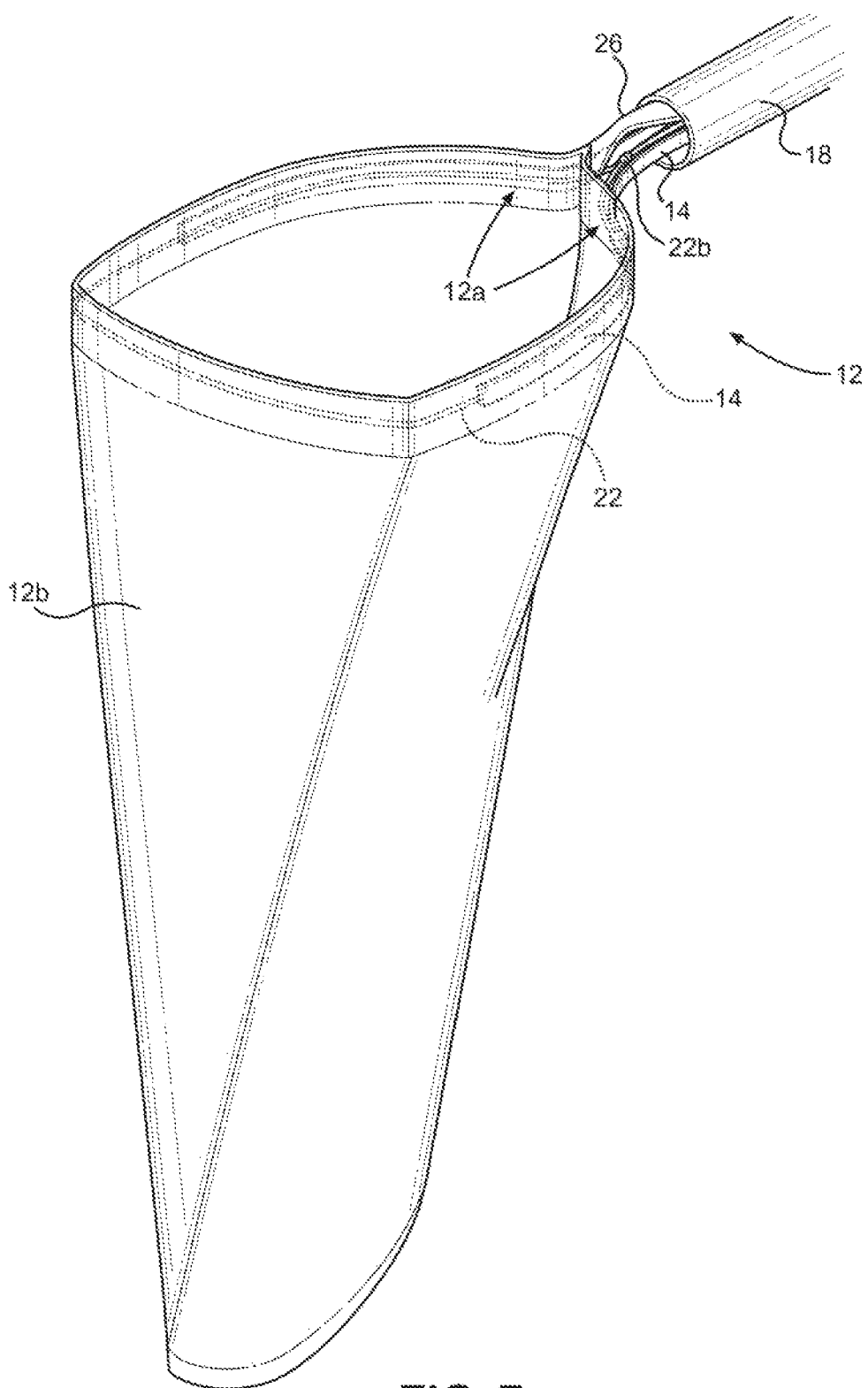
FIG. 7 is a close-up view of the bag deployed during use of the specimen retrieval system of FIG. 1.

The springs 14 are utilized to deploy or expand the bag 12 into a configuration within the surgical site suitable for collection of tissue. The springs 14 are preferably flat springs and may be made of metal and are operable to assist in keeping the bag 12 open once deployed. The springs 14 are mounted to the distal end of the interior tube 18 to maintain the springs 14 in a fixed position. Rotation of the interior tube 18 using the handle 18a enables the user to rotate the bag 12 once deployed for proper positioning of the bag 12. The interior tube handle 18a preferably has finger grooves. The distal ends of the springs 14 are located on opposite sides of the chase 12a of the basket 12b of the bag 12 to maintain the basket 12b in an open orientation, such as shown in FIG. 7. A single spring could be utilized to maintain the opening of the basket open, or to be open in a non-circular orientation. However, the use of the pair of springs is preferred.

The outer cannula 16 is configured to enable the basket 12b to be retracted therein, with the springs 14 yielding to enable the basket 12b to be withdrawing into the cannula 16. In this regard, it is noted that the bag 12 with the interior tube 18 typically does not fit through the trocar by themselves as the working area is very small. Accordingly, the outer cannula 16 with the handle 16a advantageously enables the bag 12 to be retracted when inserting the instrument through the trocar. In addition, the handle 16a is configured to provide an aperture 16b of the same size as the interior of the outer cannula 16 to permit the interior tune 18 to be inserted into the cannula 16, as seen in FIG. 2.

Figure 17:
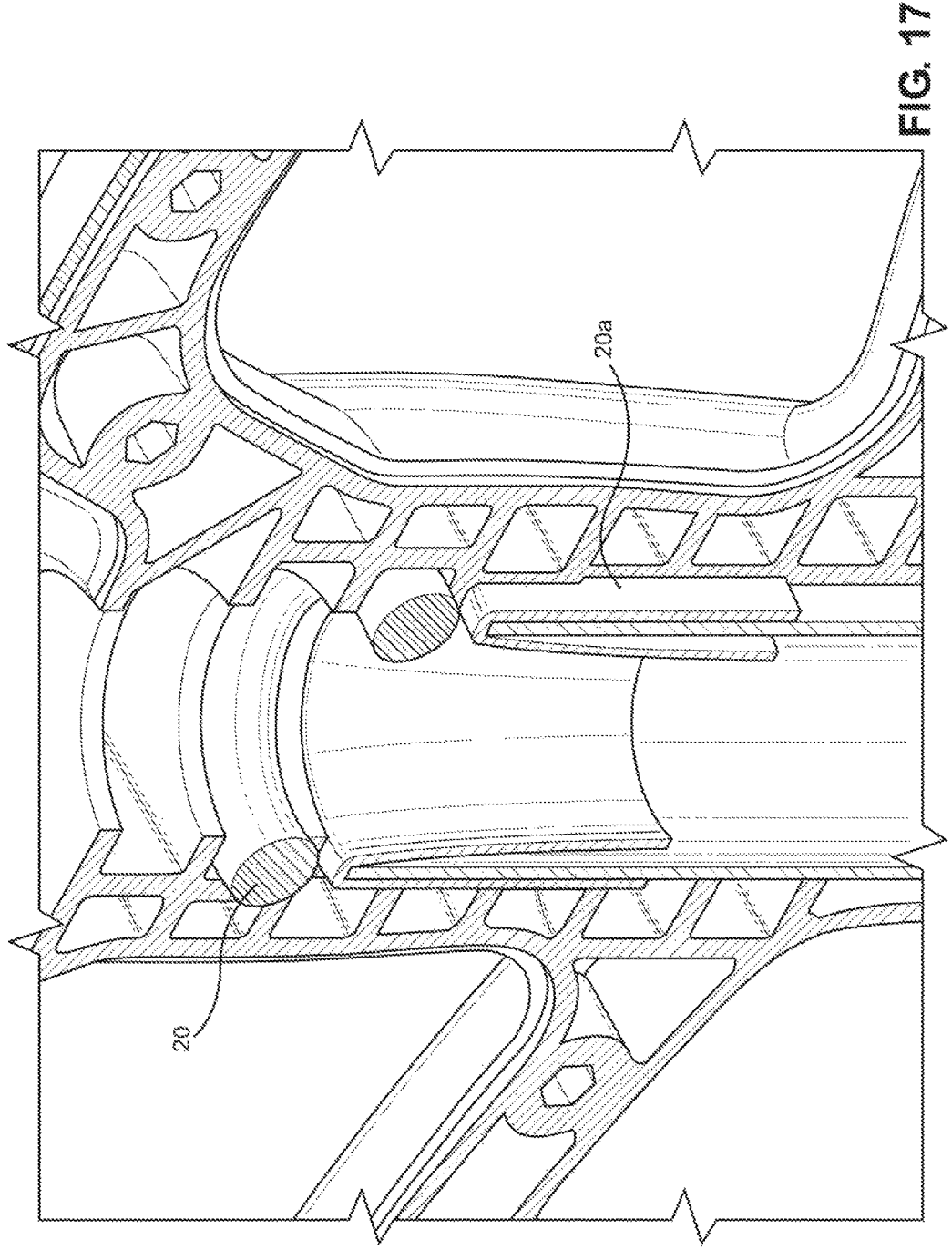
FIG. 17 shows an O-ring disposed within the handle for preventing escape of procedure inflation gas.

As seen in FIG. 17, the O-ring 20 is located within the handle 16a to press against the interior tube 18 to provide a seal to prevent procedure inflation gas from escaping during use of the system 10 in a surgical procedure. The handle 16a preferably defines an annular grove 24 configured to receive the O-ring 20 and position the O-ring 20 to slidingly engage the interior tube 18. An additional seal 20a is also preferably located on the end of the outer cannula 16 for cooperating with the O-ring 20 to provide additional sealing characteristics. The seal 20a may be a heat shrinkable tube slipped over the end of the outer cannula 16 prior to mounting of the handle 16a. About half of the length of the tube is heat shrunk onto the end of the cannula 16, and the remaining portion folded inside the cannula 16 as shown in FIG. 17.

Figure 11:
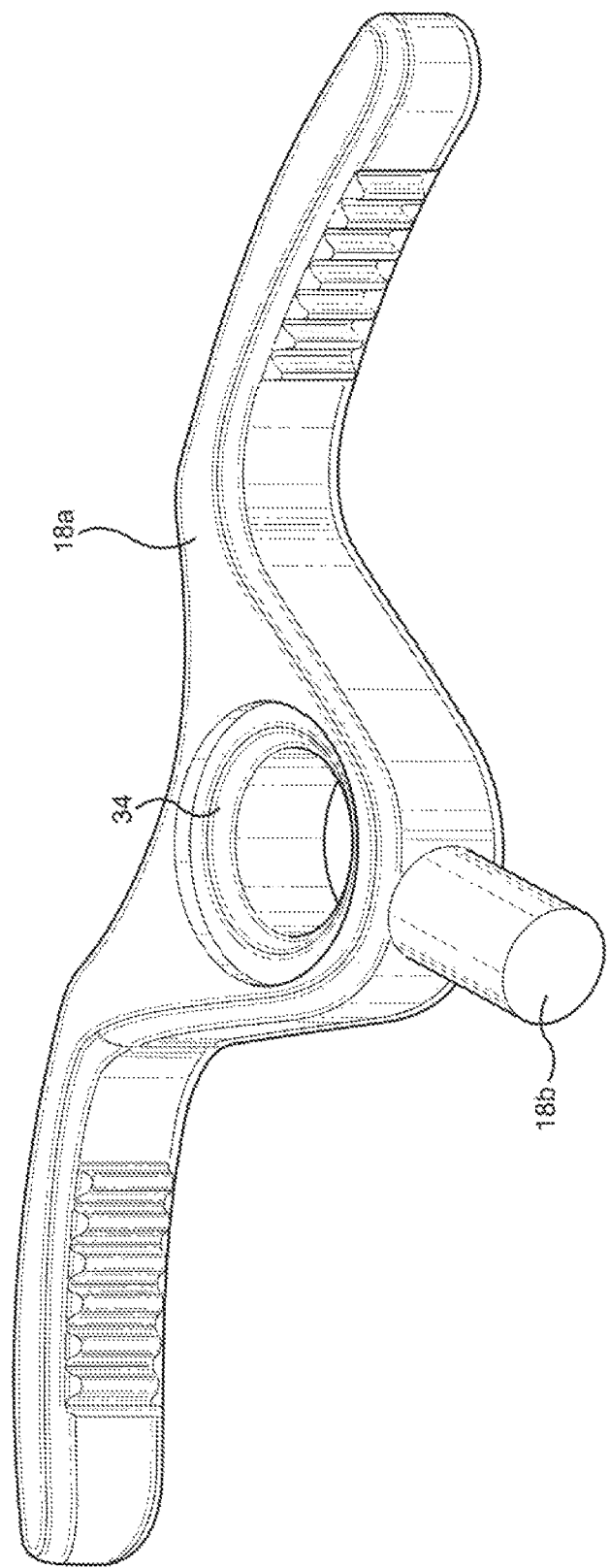
FIGS. 11 and 12 are close-up views of an interior tube handle component of the specimen retrieval system of FIG. 1.
Figure 12:
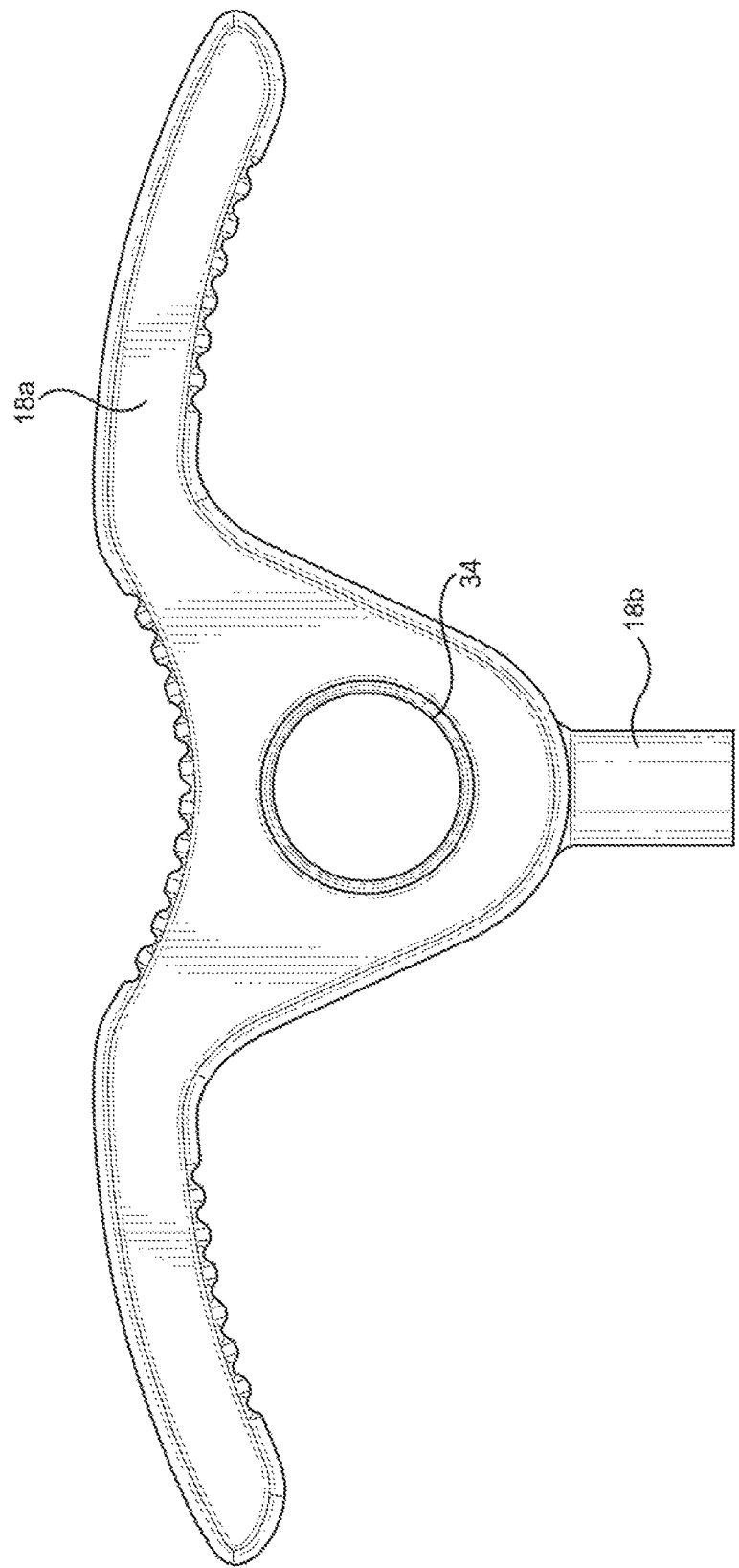
Figure 13:
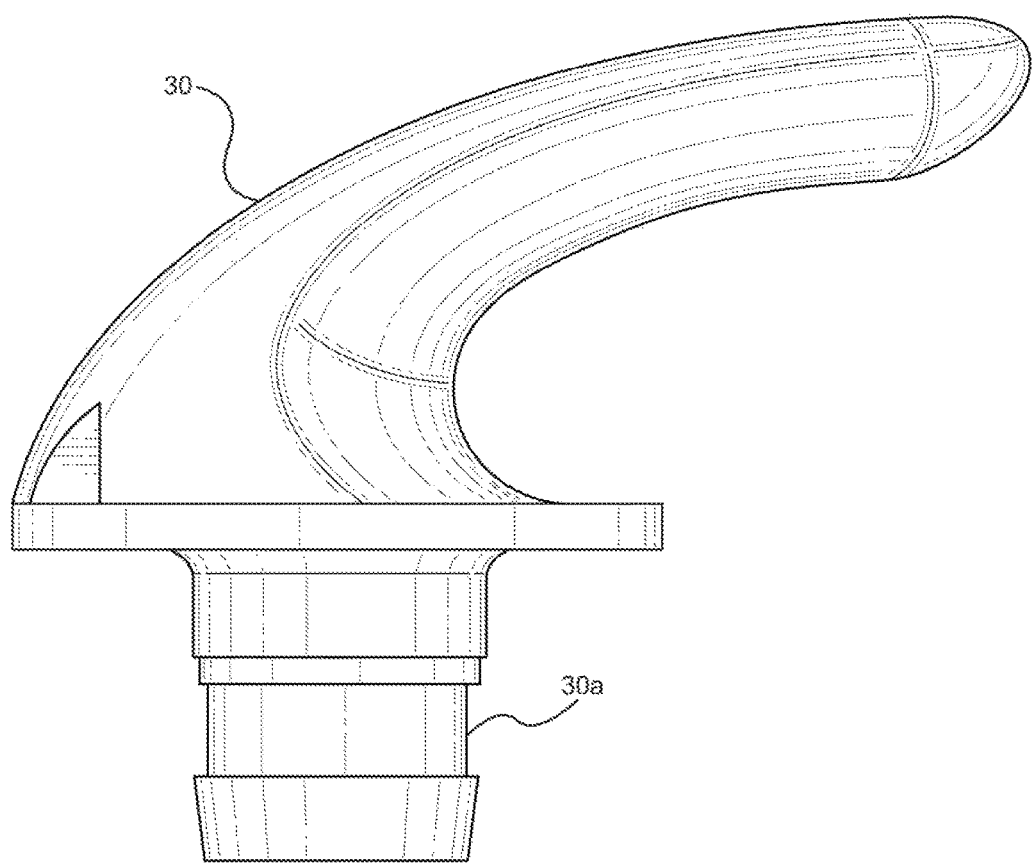
FIGS. 13 and 14 are close-up view of a rotating hook component of the specimen retrieval system of FIG. 1.
Figure 14:
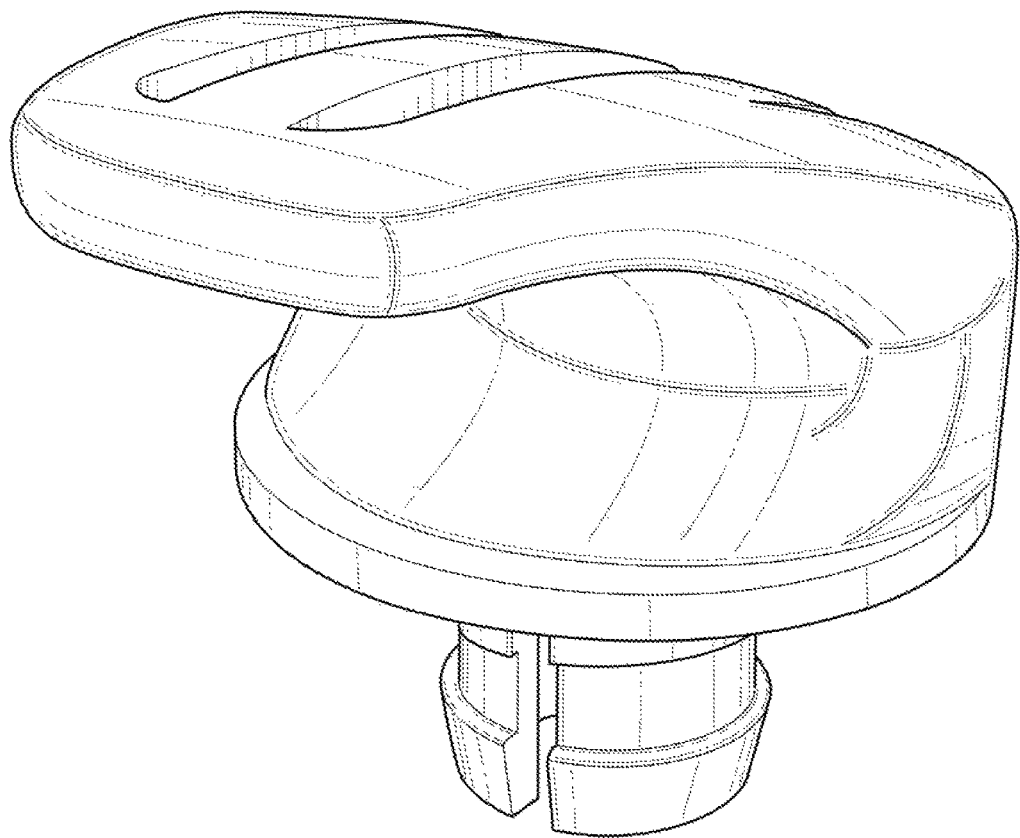
Figure 15:
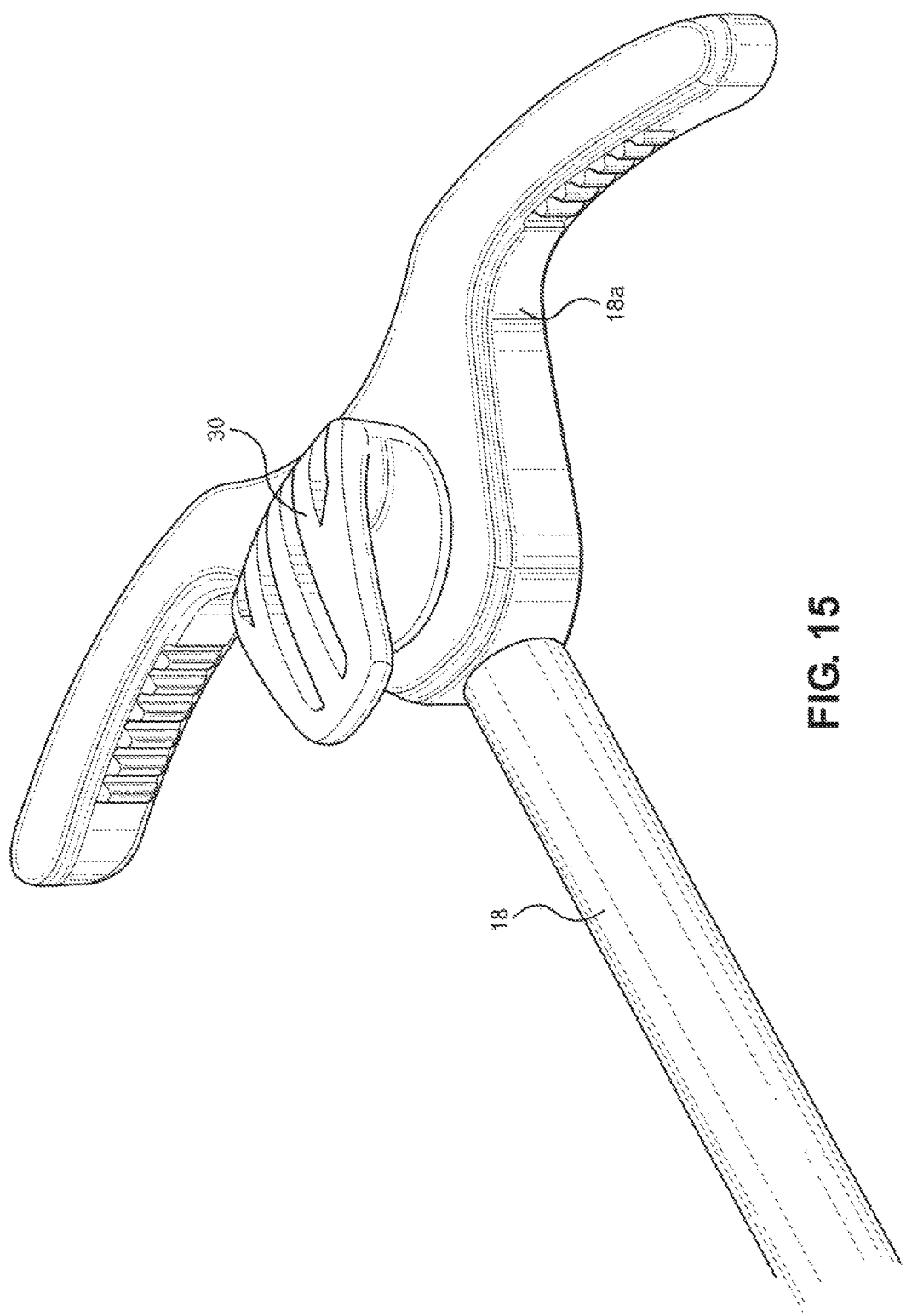
FIG. 15 is a close-up view of the interior tube, handle and rotating hook components of the specimen retrieval system of FIG. 1.
Figure 16:
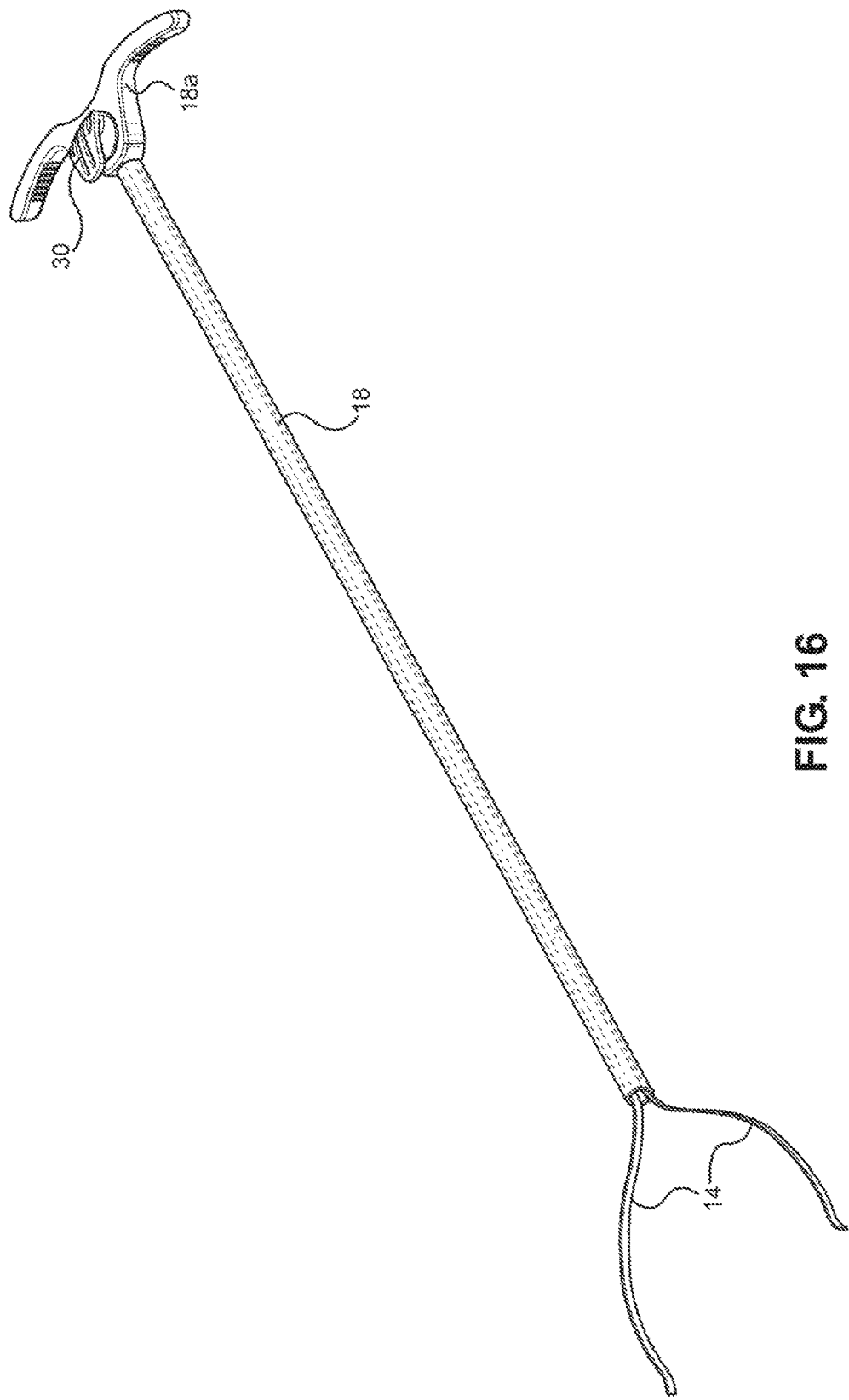
FIG. 16 shows an assembly of the interior tube, handle, and metal spring components of the specimen retrieval system of FIG. 1.

With reference to FIG. 11, the string 22 allows the user to cinch the basket 12b of the bag 12 closed after the tissue is placed inside the bag 12 and before the basket 12b and tissue are retrieved. The cinch string 22 runs through the chase 12a of the bag 12 and through an elongate tail 26 of the bag 12 located on the handle 18a. A portion of the string 22 is coated with a soft material, such as neoprene sheath 22a and looped outside the cannula 16 to provide a handle. The sheath 22a provides for comfort and to avoid medical personnel from cutting their gloves on the string 22 when grasping the string 22 to cinch the bag 12 closed. In this regard, and with additional reference to FIG. 7, the string 22 extends within the tail 26 and loops through the chase 12a of the bag 12. The distal or free end of the string 22 exiting the chase 12a of the bag 12 is tied back to the string 22 as a slip knot 22b. Thus, when the string 22 is pulled to cinch the basket 12b closed, the slip knot 22b serves to retain the basket 12b in the closed orientation. As used herein, the term string is intended to designate an elongate and thin flexible member having he characteristics of string. It will be appreciated that the term string encompasses other elongate, thin and flexible members such as ribbons, cords, lines, cables and the like.

The bag 12 can be packaged outside the outer cannula 16 or pre-rolled and retracted inside the outer cannula 16. To prevent from having memory in the material of the bag 12, The system 10 is preferably configured to package the bag 12 outside the outer cannula 16. As previously noted, the bag 12 is retracted inside the outer cannula 16 before being inserted through a trocar.

To assist in this operation, the bag 12 includes the tail 26 that is preferably stitched or otherwise affixed to the bag 12, and affixed to the handle 18a at the proximal end. The tail 26 is fixed through a primary loop 28 on the tail 26 and a hook 30 on the interior tube handle 18a. When the handle 18a is pulled, the basket 12b of the bag 12 will be retracted inside the outer cannula 16. The hook 30 preferably has a foot 30a that snap fits into an aperture 34 of the handle 18a to rotatably mount the hook 30 to the handle 18a. The handle 18a is configured to have a mount end 18b that fits into the end of the interior tube 18 to fixedly mount the handle 18a to the interior tube 18.

As noted above, the retrieval system 10 according to the disclosure is advantageously configured to enable it to be utilized using only one hand. For example, once the bag 12 is retracted, the user may prefer to deploy the bag 12 through a single handed mechanism. To assist with this, the bag 12 has a secondary free hanging user engagement structure, shown as a loop 36 located at the proximal end of the tail 26. The secondary loop 36 is configured to enable the user to exert force on the tail 26 and push down to deploy the basket 12b of the bag 12 half way.

Figure 8:
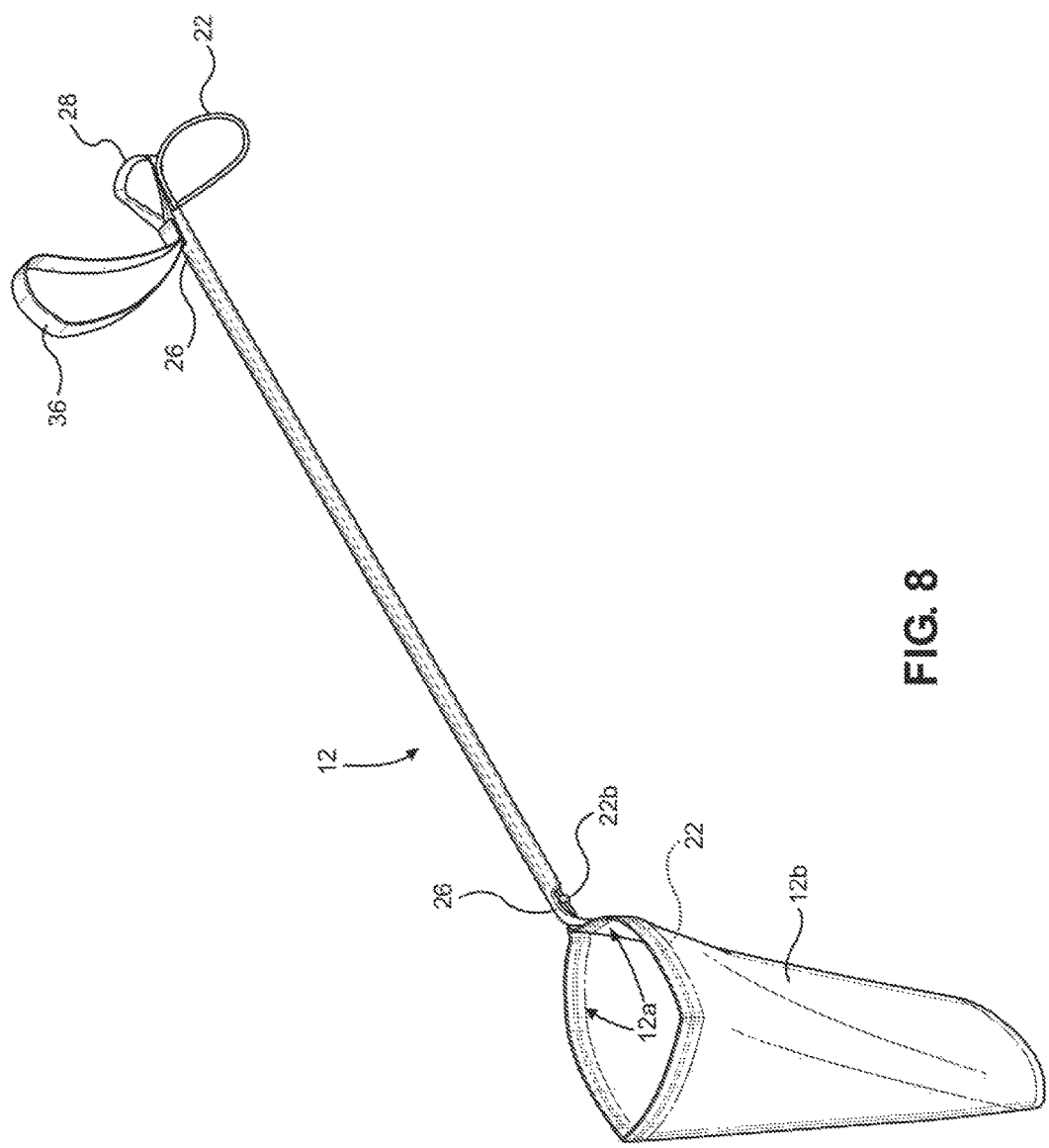
FIG. 8 is a perspective view of the bag of the specimen retrieval system of FIG. 1.
Figure 9:
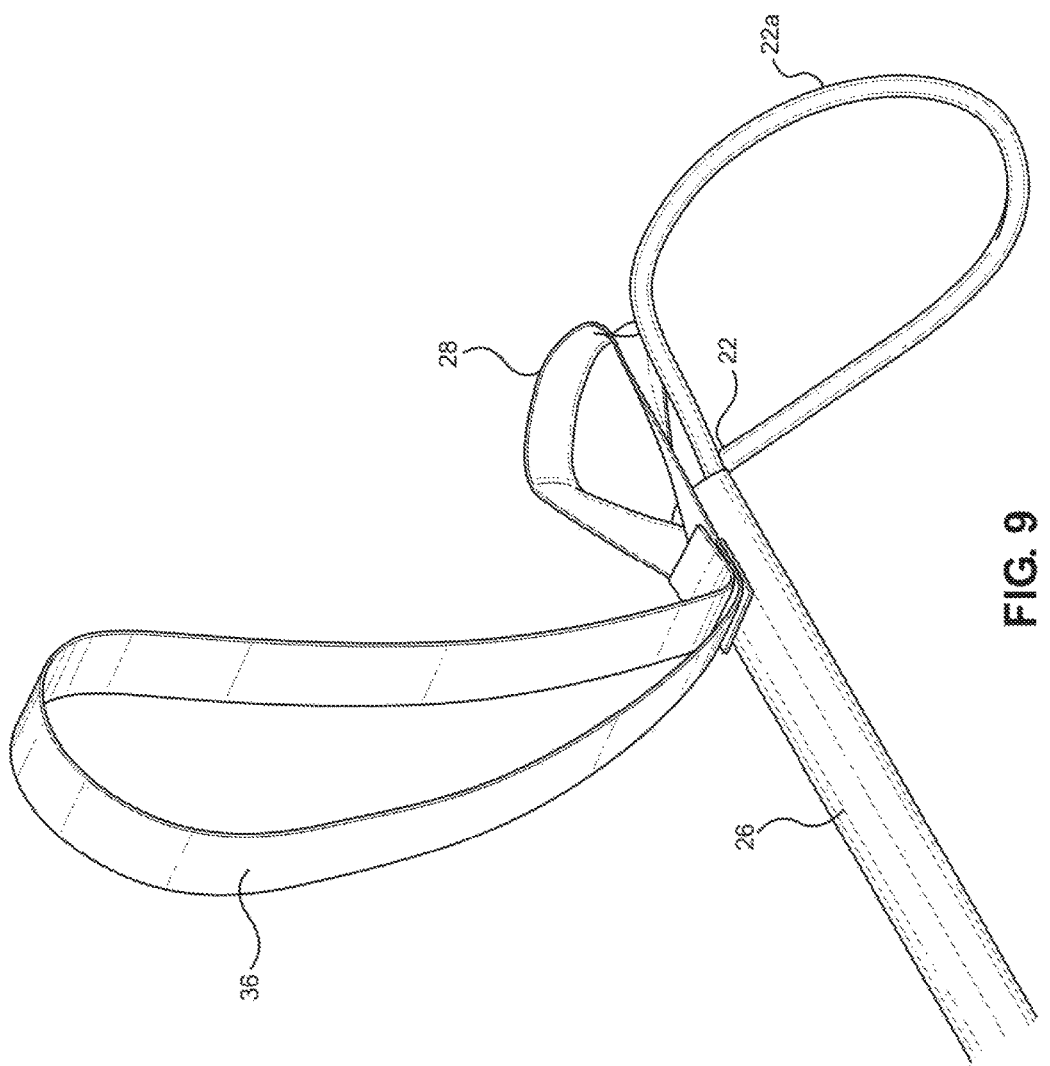
FIG. 9 is a close-up view of bag loops and cinch string components of the specimen retrieval system of FIG. 1.
Figure 10:
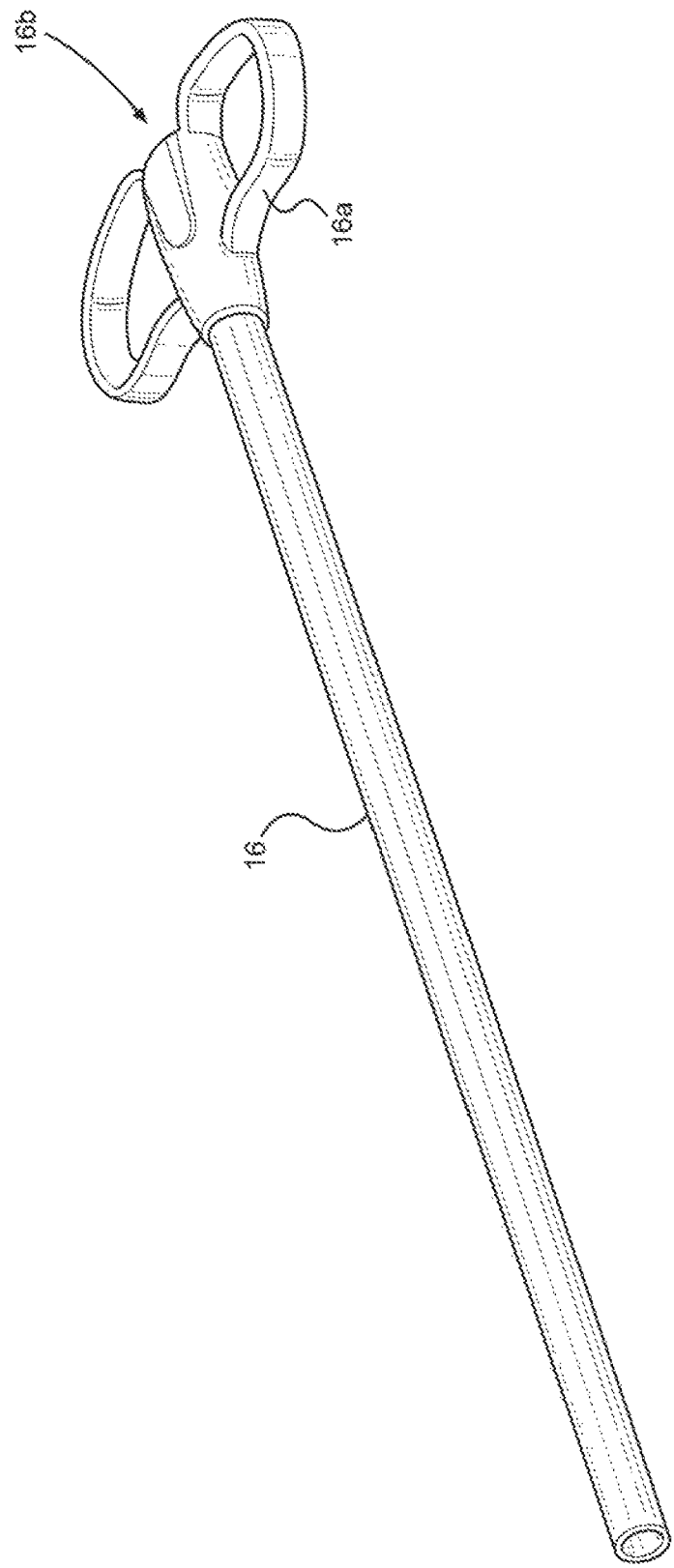
FIG. 10 shows an outer tube with the interior tube of the specimen retrieval system of FIG. 1.

For example, as seen in FIG. 3, the thumb of the user may be engaged with the secondary loop 36 and the fingers of the user engaged with the handle 16a of the outer cannula 16 to pull the interior tube 18 and urge the bag 12 toward the deployed position. Once the basket 12b of the bag 12 is deployed half way, the handle 18a is proximate the handle 16a and the user can grasp both with one hand and push on the top of the handle 18a of the interior tube 18 to fully deploy the basket 12b, as seen in FIG. 4. Thus, the inclusion of the secondary loop 36 aids in configuring the system so that the bag 12 may be deployed using a single hand. The bag 12 is shown by itself in FIG. 8, including its additional features such as the string 22, the tail 26, the primary loop 28, and the secondary loop 36.

Figure 5:
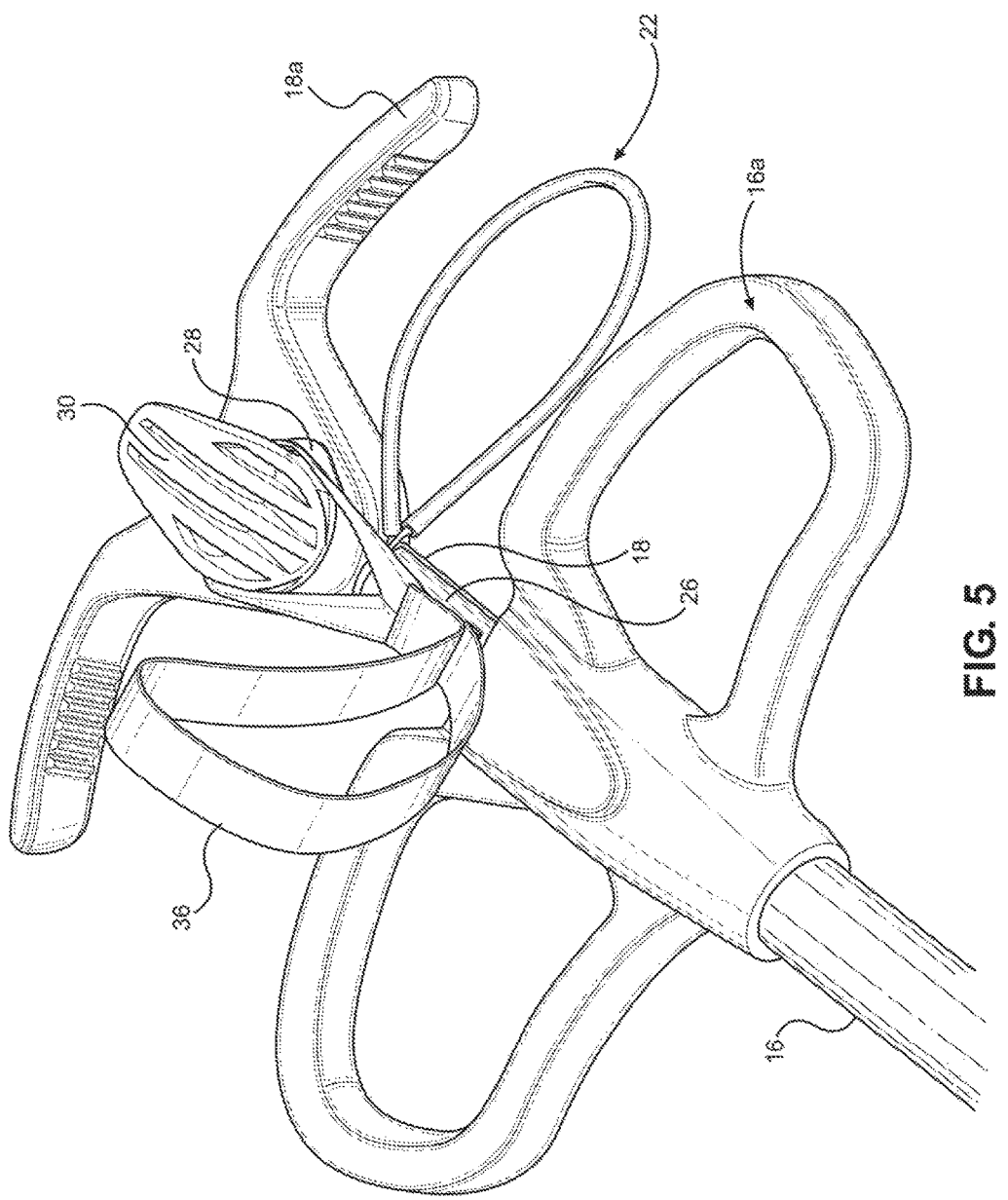
FIG. 5 shows release of the bag component during use of the specimen retrieval system of FIG. 1.
Figure 6:
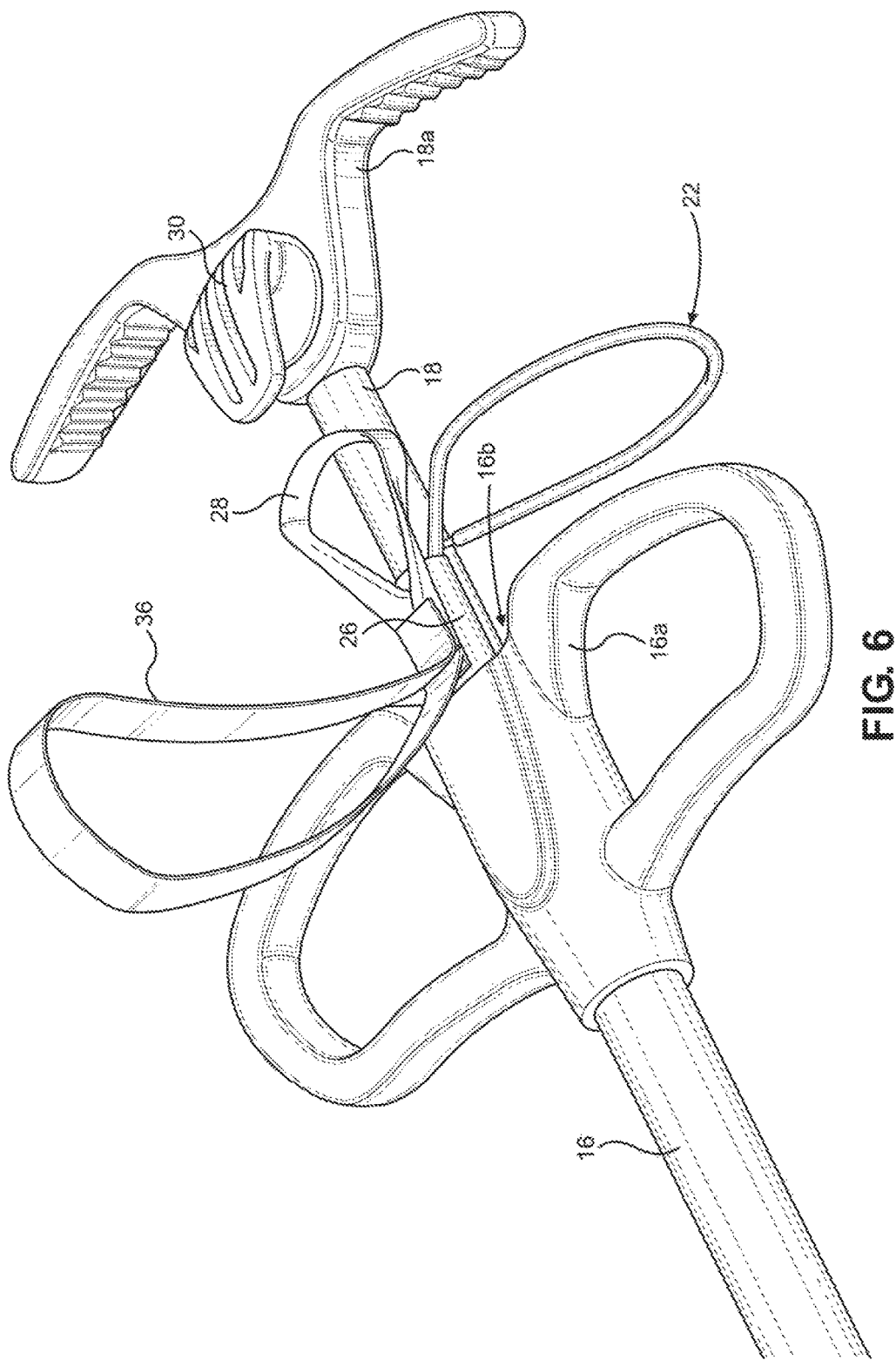
FIG. 6 shows removal of an interior tube component after release of the bag during use of the specimen retrieval system of FIG. 1.

Once the basket 12b is deployed inside the body, the user will place the compromised tissue inside the basket 12b. Once the tissue is inside the basket 12b, the user will remove the interior tube 18 and handle 18a with the distal springs 14 to release the bag 12 from the fixed assembly. As part of this, the primary loop 28 is detached from the hook 30. This detachment is achieved through the ability of the hook 30 to freely rotate about a fixed axis. As seen FIGS. 5 and 6, when the hook 30 is rotated from an upward position to a downward position, the loop 28 is able to slide off of and disengage from the hook 30. Once the interior tube 18 and handle 18a with the spring 14 is removed, the user will generally cinch the basket 12b using the string 22. Thus, inclusion of the rotatable hook 30 also aids in configuring the system to be able to be utilized using only a single hand.

Once the basket 12b is cinched, the outer cannula 16 is removed from the trocar and then the trocar is removed from the incision site. Once only the basket 12b remains, the user will generally pull the basket 12b now containing the compromised tissue out of the incision site. In this regard, it is noted that the surgeon can remove both the outer cannula 16 and the interior tube 18 during disassembly and leave the bag 12 in vivo. The string 22 will travel outside the patient and rest in the sterile field via the trocar. Once the surgeon is ready to remove the specimen, the retrieval of the compromised tissue can take place through the bag 12.

As will be appreciated, the system is advantageously configured to enable one-handed operation to facilitate deployment of the flexible basket and retrieval and closure of the flexible basket using only one hand.

The foregoing description of preferred embodiments for this disclosure has been presented for purposes of illustration and description. It is not intended to be exhaustive or to limit the disclosure to the precise form disclosed. Obvious modifications or variations are possible in light of the above teachings. The embodiments are chosen and described in an effort to provide the best illustrations of the principles of the disclosure and its practical application, and to thereby enable one of ordinary skill in the art to utilize the disclosure in various embodiments and with various modifications as are suited to the particular use contemplated.

The invention claimed is:

1. A specimen retrieval system, comprising:
a bag having a flexible basket with an opening configured for receiving a tissue specimen, an elongate tail extending from the flexible basket, a primary loop attached to a proximal end of the tail opposite the flexible basket, and a string encircling the flexible basket and extending therefrom along the tail and terminating exterior of the proximal end of the tail, the string being operable to close the opening of the flexible basket;
an outer cannula having a distal end and a proximal end with a cannula handle located at the proximal end of the outer cannula, the outer cannula configured to receive the bag therein via the distal end of the outer cannula, with the tail of the bag, the primary loop and a portion of the string extending out of the proximal end of the outer cannula; and
an interior tube having a distal end slidably positionable within the outer cannula via the proximal end of the outer cannula, the interior tube having a tube handle mounted to a proximal end of the interior tube at a location exterior of the cannula handle, the tube handle including a hook rotatably mounted thereon and configured for engaging the primary loop of the bag when rotated to a first position and configured for disengaging from the primary loop when rotated to a second position, and a spring secured within the distal end of the interior tube and extending outwardly of the distal end of the interior tube, the spring connectable to the opening of the basket of the bag.

2. The system of claim 1, further comprising a seal located within the cannula handle to contact the interior tube to provide a seal.

3. The system of claim 1, wherein the cannula handle defines an annular groove configured to receive an O-ring to contact the interior tube and provide a seal.

4. The system of claim 1, wherein the bag further includes a secondary free hanging loop located at the proximal end of the tail and configured for being engaged by a user.

5. The system of claim 1, wherein the string includes a slip knot.

6. The system of claim 1, wherein the portion of the string extending out of the proximal end of the outer cannula is configured as a loop.

7. The system of claim 1, wherein the spring comprises a pair of flat springs.

8. The system of claim 1, wherein the tail is flexible.

9. A specimen retrieval system, comprising:
a bag having a flexible basket with an opening configured for receiving a tissue specimen, an elongate tail extending from the flexible basket, a proximal end of the tail opposite the flexible basket configured for being engaged by a user, and a string encircling the flexible basket and extending therefrom along the tail and terminating exterior of the proximal end of the tail, the string being operable to close the opening of the flexible basket;
an outer cannula having a distal end and a proximal end with a cannula handle located at the proximal end of the outer cannula, the outer cannula configured to receive the bag therein via the distal end of the outer cannula, with the tail of the bag and a portion of the string extending out of the proximal end of the outer cannula; and an interior tube having a distal end slidably positionable within the outer cannula via the proximal end of the outer cannula, the interior tube having a tube handle mounted to a proximal end of the interior tube at a location exterior of the cannula handle, a spring secured within the distal end of the interior tube and extending outwardly of the distal end of the interior tube, the spring connectable to the opening of the basket of the bag, and a hook rotatably mounted on the tube handle and configured for engaging a portion of the bag when rotated to a first position and configured for disengaging from the portion of the bag when rotated to a second position.

* * * * *